United States Patent
Srinivasan et al.

(10) Patent No.: US 6,716,996 B1
(45) Date of Patent: Apr. 6, 2004

(54) PROCESS FOR PREPARING SUBSTITUTED COUMARINS

(75) Inventors: Palaniappan Srinivasan, Hyderabad (IN); Vaidya Jayathirtha Rao, Hyderabad (IN); Saravanan Chandrasekaran, Hyderabad (IN); Chandrashekar Rampally, Hyderabad (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 10/396,127

(22) Filed: Mar. 25, 2003

(51) Int. Cl.[7] ................ C07D 311/06; A61K 31/37

(52) U.S. Cl. ...................... 549/289; 514/457
(58) Field of Search .................... 549/289; 514/457

(56) References Cited

U.S. PATENT DOCUMENTS 4,788,298 A * 11/1988 Wang ................ 549/289

* cited by examiner

Primary Examiner—Alan L. Rotman
Assistant Examiner—Janet L. Coppins
(74) Attorney, Agent, or Firm—Ladas & Parry

(57) ABSTRACT

The present invention relates to a process for preparing substituted coumarins. More particularly, the present invention relates to a process for preparing substituted coumarins using polyaniline salts as catalysts.

10 Claims, No Drawings

PROCESS FOR PREPARING SUBSTITUTED COUMARINS

FIELD OF THE INVENTION

The present invention relates to a process for preparing substituted coumarins. More particularly, the present invention relates to a process for preparing substituted coumarins using polyaniline salts as catalysts.

BACKGROUND OF THE INVENTION

Coumarins are an important group of naturally occurring compounds, widely distributed in the plant kingdom and have been produced synthetically for many years for commercial use. Members of this group display a broad range of applications—as fragrances, pharmaceuticals, additives to food, cosmetics, agrochemicals, optical brightening agents, dispersed fluorescent and tunable dye lasers, and biological activities like anthelmintic, hypnotic, insecticidal and anticoagulant properties. Coumarins also act as intermediates for the synthesis of fluorocoumarins, chromones, coumarones, and 2-acylresorcinol. [See—Boisde et al, Kirk-Othmer Encyclopedia of Chemical Technology (Ed, Jacqline I. Kroschwitz), $4^{th}$ Edition, Vol.7, Pages 647–658 and references therein]. Coumarin and some of its derivatives have been identified in plants and many of them have been synthesized and studied for their physiological activity. 7-hydroxy coumarin, known as umbelliferone, occurs naturally in gum resins of Umbelliferae and is an important coumarin metabolite. It is readily manufactured from resorcinol and maleic or fumaric acid. Derivatives of umbelliferone have attracted interest as sunburn preventives on account of their wide spectrum of UV absorption.

7-hydroxy-4-metylcoumarin ($\beta$-methylumbelliferone) is used as fluorescent brightener, efficient laser dye for pulsed and SW operation, standard for the flurometric determination of enzyme activity, as a starting material for the preparation of an insecticide (Hymerocromone), as precursor for furano coumarins and many other derivatives of substituted coumarins and as analytical reagents. 5,7-dihydroxy-4-methylcoumarin is used in suntan oils as sunscreen, and in wall paints as whitening agents. Coumarin and its derivatives can be synthesized by various methods which include Perkin reaction (Donnelly et al, Tetrahedron, 1968, vol 24, p-2617–2622), Knoevenagel reaction (Franca Bigi et al, J. Org. Chem., 1999, vol 64, p-1033–1035), Wittig reaction (Yavari et at, Tetrahedron Lett., 1998, vol 39, p-2391–2392), Pechmann reaction (John et al, J. Org. Chem., 1961, vol 26, p-240–242) and Reformatsky reaction. Among these methods, Pechmann reaction is the most widely used method for the preparation of substituted coumarins since it proceeds from very simple starting materials and gives good yields of various substituted coumarins.

Substituted coumarins have been prepared using various reagents such as $H_2SO_4$, $POCl_3$ (Ahmad et al, Proc. Indian Acad. Sci., 1937, vol.5A, p-277–284), $AlCl_3$ (Das gupta et al, J. Chem. Soc., 1969, p-29–33), Cation exchange resins (John et al, J. Org. Chem, 1961, vol 26, p-240–242), trifluoro acetic acid (Woods et al, J. Org. Chem., 1962, vol 27, p-3703–3705), Montmorillonite clay (Bhattacharyya et al, Ind. J. Chem., 1992, vol 31B, p628), solid acid catalysts (Bekkum et al, J. Chem. Soc., Chem. Commun., 1995, p-225–226), $W/ZrO_2$ solid acid catalyst (Reddy et al, Synth. Commun., 2001, vol 31 (23), p-3603–3607), Chloroaluminate ionic liquid (Khadilkar et al, Synlett, 2002, No 1, p-152–154) and Nafion-H catalyst (Chaudhari, Chem. Ind., 1983, p-569–570).

Condensation is one of the most fundamental and important reactions in organic synthesis. Conventionally, the processes of making coumarins can be carried out by:

(a) Liquid-phase reaction utilizing a liquid catalyst: This type of process utilizes liquid phase acids, such as sulfuric acid, phosphoric acid, or sulfonic acid, as catalysts.

(b) Liquid phase reaction utilizing a solid catalyst: This type of processes typically utilizes inorganic salts, cation exchange resin and solid acid catalyst etc.

One problem associated with liquid-phase reaction using liquid-catalyst, is that the acidic catalysts of sulfuric acid or sulfonic acid can cause corrosion problems to the reactor. These liquid acid catalysts are also discharged along with reaction products, thus causing sever waste disposal and pollution problems.

The drawback of using mineral acids as catalysts are: (i) Catalyst can not be reused, (ii) Disposal of acid is not environmentally safe and it is not economical, (iii) Low selectivity is frequently observed, (iv) Corrosion of the reaction vessel and reactors, (v) Not easy to handle and (vi) High inventory of the catalyst.

The solid-catalyst in liquid-phase reaction, which typically utilizes a cation exchange resin as catalyst, ameliorates the corrosion and waste disposal problems experienced with the liquid-catalyst in liquid-phase processes, and results in simplified separation procedure required between the reaction product and catalysts. However, cation exchange resins typically exhibit relatively poor heat-resistance, and they often lose substantial activity after being subject to heat. Once the catalytic activity of the cation exchange resins is reduced, it is difficult to be regenerated.

OBJECTS OF THE INVENTION

The main object of the present invention is to provide a process for the preparation of substituted coumains using polyaniline salts as catalysts, which obviates the drawbacks as detailed above.

SUMMARY OF THE INVENTION

Accordingly, the present invention relates to a process for the preparation of substituted coumarin using polyaniline salts as catalysts, which comprises the reaction between phenols and keto esters in presence of catalysts in the temperature range from 110 to 170° C. for the period of 3 to 24 hrs., separating the product by conventional method from the reaction mixture.

In an embodiment of the present invention, the phenols used is selected from resorcinol, phloroglucinol and pyrogallol.

In an another embodiment of the present invention, the keto esters used is selected from methyl acetoacetate, ethyl acetoacetate and phenyl acetoacetate.

In an yet another embodiment of the present invention, the catalysts is a polyaniline salt selected from polyaniline-sulfate, polyaniline-hydrochloride, polyaniline-nitrate, polyaniline-perchlorate, polyaniline-sodium bisulfate, polyaniline-p-toluene sulfonate, polyaniline-trifluoroacetate and polyaniline-sulfosalicylate system.

In still yet another embodiment of the present invention, the reaction is carried out in the temperature range from 110 to 170° C.

In still yet another embodiment of the present invention, the reaction is carried out for a period of 3 to 24 hrs.

In still yet another embodiment of the present invention, the catalyst amount used is 10% to 30% with respect to phenols.

In still yet another embodiment of the present invention, the amount of keto ester used is 1, 1.2, 1.5, 2.0, 3.0 equivalent with respect to one equivalent of phenols.

In still yet another embodiment of the present invention, the solvent is selected from toluene, xylene, chlorobenzene and p-chloro toluene.

DETAILED DESCRIPTION OF THE INVENTION

These embodiments will be apparent from the ensuing detailed description of the present invention.

The process of preparation of substituted coumarins is carried out by reacting phenols with keto esters in presence of catalyst and then removing the catalyst by conventional methods. The substituted coumarins can be isolated such as filtration followed by isolation of product by conventional methods.

The novelty of the invention resides in the use of polyaniline salt as catalyst in the preparation of substituted coumarins. The use of polyaniline salts as catalysts provides the following advantages: (i) separation of catalyst from a reaction mixture is easy, (ii) repeated use of catalyst is possible, (iii) there is no problem for the disposal of used catalyst as they are environmentally safe and (iv) preparation of the catalyst is a straight forward synthetic route.

The following examples are given by way of illustration and therefore should not be construed as limit the scope of the present invention.

EXAMPLE 1

The following example illustrates preparation of polyaniline-sulfate salt using benzoyl peroxide. 4.85 g of benzoyl peroxide was dissolved in 150 ml acetone. To this solution, 1.44 g of sodium lauryl sulfate in 25 ml distilled water was added. 2.4 ml aniline in 30 ml aqueous solution containing sulfuric acid (9.0 ml) was introduced drop wise into the above solution at 35° C. and stirred the mixture for 8 h. Precipitated polyaniline salt was filtered off, and then washed with 3 L of distilled water, followed by methanol. Resulting polymer salt was finally dried at 100° C. until a constant mass was reached.

EXAMPLE 2

The following example illustrates preparation of different polyaniline salts from polyaniline base. In a typical experiment, polyaniline-sulfate salt prepared using example 1 was constantly stirred in 1 M NaOH for 8 h, filtered, washed with water and finally dried at 100° C. till a constant mass. Dedoped polyaniline base (0.5 gm) was introduced into the 50 ml acid solution (1 M) and the mixture left stirring at constant temperature for 4 h. The polyaniline salt was filtered and then washed with distilled water until the washing liquid was colorless. Finally, the resulting polymer salt was washed with acetone and subsequently dried at 100° C. till a constant mass. Acid used and the corresponding polyaniline salts are given in Table I.

TABLE I

| ACID | POLYANILINE SALT |
| --- | --- |
| Sulfuric acid | Polyaniline-sulfate |
| Hydrochloric acid | Polyaniline-hydrochloride |
| Nitric acid | Polyaniline-nitrate |
| Perchloric acid | Polyaniline-perchlorate |

TABLE I-continued

| ACID | POLYANILINE SALT |
| --- | --- |
| Sodium bisulfate | Polyaniline-sodium bisulfate |
| p-toluene sulfonic acid | Polyaniline-p-toluene sulfonate |
| Trifluoro acetic acid | Polyaniline-trifluoroacetate |
| 5-Sulfosalicylic acid | Polyaniline-sulfosalicylate |

EXAMPLE 3

The following example illustrates the preparation of different grade of polyaniline-sulfate salts from polyaniline base using different amount of sulfuric acid. In a typical experiment polyaniline-sulfate salt prepared using example 1 was constantly stirred in 1 M NaOH for 8 h, filtered, washed with water and finally dried at 100° C. till a constant mass. The dedoped polyaniline base (0.5 gm) was introduced into different concentration of sulfuric acid (0.1, 1.0, 3.0 and 5.0 M) and the mixture left under stirring at constant temperature for 4h. Polyaniline salt was filtered and then washed with distilled water until washing liquid was colorless. Finally, resulting polymer salt was washed with acetone and subsequently dried at 100° C. till a constant mass.

EXAMPLE 4

Following example illustrates preparation of polyaniline-sulfate salt using different oxidizing agents. In a typical experiment, aqueous solution of oxidizing agent (0.1 M) was added very slowly into 1.0M $H_2SO_4$ acid solution containing 0.1 M aniline at a temperature of 0–5° C. After all the oxidant was added, the reaction mixture was so at constant temperature for 4 hours. The oxidation of aniline is highly exothermic and, therefore, the rate of addition of the oxidant was adjusted to prevent any increase in the temperature of the reaction mixture. Precipitated polyaniline was filtered and then washed with distilled water until washing liquid was colorless. In order to remove oligomers and other organic by products, precipitate was washed with methanol until the methanol solution was colorless. Finally, resulting polymer salt was washed with acetone and subsequently dried at 100° C. till a constant mass. Oxidizing ants used in reaction are given in Table II.

TABLE II

| OXIDIZING AGENT USED IN THE REACTION |
| --- |
| Ammonium persulfate |
| Potassium dichromate |
| Sodium persulfate |
| Potassium persulfate |

Catalyst (polyaniline salt) was heated at 100°C. for 3 h and used in the reaction of phenols with keto esters.

EXAMPLE 5

Following example illustrates preparation of 7-hydroxy-4-methylcoumarin with different reaction times. In a typical experiment, resorcinol (1.0 g, 9.1 mmol) was taken in 10 ml round bottomed flask and ethyl acetoacetate (2.37 g, 18.2 mmol) was added followed by 200 mg of polyaniline-sulfate salt catalyst powder (20 wt % with respect to resorcinol) prepared using example 1. Reaction mixture was refluxed at 150° C. for different intervals of time. Reaction mixture was washed with acetone, filtered and acetone was evaporated under vacuum. The product obtained was washed with water, filtered and dried at 100° C. Product was purified by dissolving in 1.0N NaOH solution and then regenerated with 1.0N $H_2SO_4$ solution. Precipitated product was filtered, washed with water and sample was dried at 100° C. till a constant mass. Product was characterized by $^1H$ NMR spectrum. Yield of the product is given in Table III.

TABLE III

| REACTION TIME (h.) | YIELD (%) |
|---|---|
| 4 | 54 |
| 6 | 72 |
| 9 | 75 |
| 24 | 72 |

EXAMPLE 6

The following example illustrates the preparation of 7-hydroxy-4-methylcoumarin with different amounts of catalyst. In an experiment, resorcinol (1.0 g, 9.1 mmol) was taken in 10 ml round bottomed flask and ethyl acetoacetate (2.37 g, 18.2 mmol) was added followed by different amounts of polyaniline-sulfate salt catalyst powder prepared using example 1. The reaction mixture was refluxed at 150° C. for 6 h. Isolation and purification of the product was carried out as reported in example 5. The yield of the product is given in Table IV.

TABLE IV

| AMOUNT OF CATALYST (mg.) | YIELD (%) |
|---|---|
| 100 | 65 |
| 150 | 70 |
| 200 | 72 |
| 300 | 72 |

EXAMPLE 7

The following example illustrates the preparation of 7-hydroxy-4-methylcoumarin with different amounts of ethyl acetoacetate. In an experiment, resorcinol (1.0 g, 9.1 mmol) was taken in 10 ml round bottomed flask and different amounts of ethyl acetoacetate was added followed by 200 mg of polyaniline-sulfate salt catalyst powder prepared using example 1. The reaction mixture was refluxed at 150° C. for 6 h. Isolation and purification of product was cared out as reported in example 5. Yield of the product is given in Table V.

TABLE V

| RESORCINOL: ETHYL ACETOACETATE (MOLE RATIO) | YIELD (%) |
|---|---|
| 1.0 : 1.0 | 41 |
| 1.0 : 1.2 | 54 |
| 1.0 : 1.5 | 62 |
| 1.0 : 2.0 | 72 |
| 1.0 : 3.0 | 75 |

EXAMPLE 8

The following example illustrates the preparation of 7-hydroxy-4-methylcoumarin with different temperatures. Resorcinol (1.0 g, 9.1 mmol) was taken in 10 ml round bottomed flask and ethyl acetoacetate (2.37 g, 18.2 mmol) was added followed by 200 mg of polyaniline-sulfate salt catalyst powder prepared using example 1. Reaction mixture was refluxed at different temperatures for 6 h. Isolation and purification of the product was carried out as reported in example 5. The yield of the product is given in Table VI.

TABLE VI

| TEMPERATURE (° C.) | YIELD (%) |
|---|---|
| 110 | 4 |
| 130 | 34 |
| 150 | 72 |
| 170 | 74 |

EXAMPLE 9

The following example illustrates the preparation of 7-hydroxy-4-methylcoumarin using the recovered catalyst for five times. Resorcinol (3.0 g, 27.3 mmol) was taken in 25 ml round bottomed flask and ethyl acetoacetate (7.11 g, 54.6 mmol) was added followed by 600 mg of polyaniline-sulfate salt catalyst powder prepared using example 1. The reaction mixture was refluxed at 150° C. for 6 h. Isolation and purification of the product was carried out as reported en example 5. The experiment was carried out five times more using the recovered catalyst. The yield of the product is given in Table VII.

TABLE VII

| REPEATABILITY (NUMBER OF TIME) | YIELD (%) |
|---|---|
| First | 70 |
| Second | 68 |
| Third | 69 |
| Fourth | 67 |
| Fifth | 68 |
| Sixth | 68 |

EXAMPLE 10

The following example illustrates the preparation of 7-hydroxy-4-methylcoumarin using different polyaniline salts. Resorcinol (1.0 g, 9.1 mmol) was taken in 10 ml of bottom flask and ethyl acetoacetate (2.37 g, 18.2 mmol) was added followed by 200 mg of different polyaniline salt catalyst powder prepared using example 2. The reaction mixture was refluxed at 150° C. for 6 h. Isolation and purification of the product was carried out as reported in example 5. The yield of the product is given in Table VIII.

TABLE VIII

| POLYANILINE SALT | YIELD (%) |
|---|---|
| Polyaniline-hydrochloride | 12 |
| Polyaniline-sulfate | 70 |
| Polyaniline-nitrate | 6 |
| Polyaniline-perchlorate | 72 |
| Polyaniline-sodium bisulfate | 26 |
| Polyaniline-p-toluene sulfonate | 62 |
| Polyaniline-trifluoroacetate | 20 |
| Polyaniline-sulfosalicylate | 67 |

EXAMPLE 11

The following example illustrates the preparation of 7-hydroxy-4-methylcoumarin using polyaniline-sulfate salts prepared using different oxidizing agents. Resorcinol (1.0 g, 9.1 mmol) was taken in 10 ml round bottom flask and ethyl acetoacetate (2.37 g. 18.2 mmol) was added followed by 200 mg of different polyaniline salt catalyst powder prepared using example 4. The reaction mixture was refluxed at 150° C. for 6 h. Isolation and purification of the product was carried out as reported in example 5. Yield of product is given in Table IX.

TABLE IX

| POLYANILINE-SULFATE SALT PREPARED USING DIFFERENT OXIDIZING AGENT | YIELD (%) |
|---|---|
| Ammonium persulfate | 71 |
| Sodium persulfate | 62 |
| Potassium dichromate | 60 |
| Benzoyl peroxide | 72 |

EXAMPLE 12

The following example illustrates preparation of 5,7-dihydroxy-4-methylcoumarin using different reaction times. Phloroglucinol (0.63 g, 5.0 mmol) was taken in 10 ml round bottomed flask and ethyl acetoacetate (1.3 g, 10.0 mmol) was added followed by 126 mg of polyaniline-sulfate salt catalyst powder prepared using example 1. The reaction mixture was refluxed at 150° C. for different intervals of time. Isolation and purification of the product was carried out as reported in example 5. The yield of the product is given in Table X.

TABLE X

| REACTION TIME(hrs) | YIELD (%) |
|---|---|
| 3 | 55 |
| 6 | 71 |
| 8 | 75 |
| 10 | 71 |
| 20 | 71 |

EXAMPLE 13

The following example illustrates the preparation of 5,7-dihydroxy-4-methylcoumarin with different amounts of catalyst. Phloroglucinol (0.63 g, 5.0 mmol) was taken in 10 ml round bottomed flask and ethyl acetoacetate (1.3 g, 10.0 mmol) was added followed by different amounts of polyaniline-sulfate salt catalyst powder prepared using example 1. The reaction mixture was refluxed at 150° C. for 6 h. Isolation and purification of the product was carried out as reported in example 5. Yield of product is given in Table XI.

TABLE XI

| AMOUNT OF CATALYST(mg) | YIELD (%) |
|---|---|
| 63 | 68 |
| 95 | 70 |
| 126 | 71 |
| 189 | 78 |

EXAMPLE 14

The following example illustrates the preparation of 5,7-dihydroxy-4-methylcoumarin with different amounts of ethyl acetoacetate. Phloroglucinol (0.63 g, 5.0 mmol) was taken in 10 ml round bottomed flask and different amounts of ethyl acetoacetate was added followed by 126 mg of polyaniline-sulfate salt catalyst powder prepared using example 1. Reaction mixture was refluxed at 150° C. for 6 h. Isolation and purification of product was carried out as reported in example 5. Yield of the product is given in Table XII.

TABLE XII

| PHLOROGLUCINOL: ETHYL ACETOACETATE (MOLE RATIO) | YIELD (%) |
|---|---|
| 1.0:1.0 | 61 |
| 1.0:1.5 | 70 |
| 1.0:2.0 | 71 |
| 1.0:3.0 | 69 |

EXAMPLE 15

The following example illustrates preparation of 5,7-dihydroxy-4-methylcoumarin with different grade of polyaniline-sulfate salt prepared using different amounts of sulfuric acid. Phloroglucinol (0.63 g, 5.0 mmol) was taken in 10 ml round bottomed flask and ethyl acetoacetate (1.3 g, 10.0 mmol) was added followed by 126 mg of polyaniline-sulfate salt catalyst powder prepared using example 3. The reaction mixture was refluxed at 150° C. for 6 h. Isolation and purification of the product was carried out as reported in example 5. The yield of the product is given in Table XIII.

TABLE XIII

| CONCENTRATION (M) OF SULFURIC ACID USED | YIELD (%) |
|---|---|
| 0.1 | 33 |
| 1.0 | 33 |
| 3.0 | 58 |
| 5.0 | 52 |

EXAMPLE 16

The following example illustrates the preparation of substituted coumarins using polyaniline-sulfate salt. In an experiment, phenols (one equivalent) was taken in 10 ml rounded bottomed flask and keto esters (two equivalent) was added followed by polyaniline-sulfate salt catalyst powder (20 wt % with respect to phenols) prepared using example 1. The reaction mixture was refluxed at 150° C. for 6 h. Isolation and purification of the product was carried out as reported in example 5. The yield of the product is given in Table XIV.

TABLE XIV

| PHENOLS | KETO ESTER | PRODUCT | YIELD % |
|---|---|---|---|
| Resorcinol | Methyl acetoacetate | 7-hydroxy-4-methylcoumarin | 78 |
| Phloroglucinol | Methyl acetoacetate | 5,7-dihydroxy-4-methylcoumarin | 70 |
| Pyrogallol | Methyl acetoacetate | 7,8-dihydroxy-4-methylcoumarin | 44 |
| Resorcinol | Ethyl acetoacetate | 7-hydroxy-4-methylcoumarin | 72 |
| Phloroglucinol | Ethyl acetoacetate | 5,7-dihydroxy-4-methylcoumarin | 71 |
| Pyrogallol | Ethyl acetoacetate | 7,8-dihydroxy-4-methylcoumarin | 32 |

EXAMPLE 17

The following example illustrates the preparation of 5,7-dihydroxy-4-methyl coumarin using different solvents. In a typical experiment, phloroglucinol (0.63 g, 5.0 mmol) was taken in 50 ml round bottomed flask and ethyl acetoacetate (1.3 g, 10.0 mmol) was added followed by 20 ml of solvent. Polyaniline-sulfate salt catalyst powder (63 mg) prepared using example 1 was added in to the above mixture. Reaction mixture was refluxed for 24 h. Isolation and purification of the product was carried out as reported in example 5. The yield of the product is given in Table XV.

TABLE XV

| SOLVENT | YIELD (%) |
|---|---|
| Toluene | 55 |
| Xylene | 53 |
| Chlorobenzene | 28 |

The main advantages of the present invention are:

The use of polyaniline-salts as catalysts in the preparation of substituted coumarins for the first time. The use of polyaniline salts as catalysts provides the following advantages (i) separation of catalyst from a reaction mixture is easy, (ii) repeated use of catalyst is possible, (iii) there is no problem for the disposal of used catalyst as they are environmentally safe, though the disposal of mineral acid catalyst requires much money for treatment to make it environmentally safe, and (iv) preparation of the catalyst is straight forward synthetic route.

In view of the above, it will be seen that several advantages of the invention are achieved and other advantageous results attained. As various changes could be made in the above methods and compositions without departing from the scope of the invention, it is intended that all matter contained in the above description shall be interpreted as illustrative and not in a limiting sense.

We claim:

1. A process for the preparation of substituted coumarins, which comprises reacting a phenol with a keto ester in the presence of a catalyst comprising a polyaniline salt, and then separating the substituted coumarin obtained from the reaction mixture.

2. A process as claimed in claim 1 wherein the phenol is selected from the group consisting of resorcinol, phloroglucinol and pyrogallol.

3. A process as claimed in claim 1 wherein the keto ester is selected from the group consisting of methyl acetoacetate, ethyl acetoacetate and phenyl acetoacetate.

4. A process as claimed in claim 1 wherein the polyaniline salt catalyst is selected from the group consisting of polyaniline-sulfate, polyaniline-hydrochloride, polyaniline-nitrate, polyaniline-perchlorate, polyaniline-sodium bisulfate, polyaniline-p-toluene sulfonate, polyaniline-trifluoroacetate and polyaniline-sulfosalicylate system.

5. A process as claimed in claim 1 wherein the reaction is carried out at a temperature in the range of 110 to 170° C.

6. A process as claimed in claim 1 wherein the reaction is carried out for a time period in the range of 3 to 24 hrs.

7. A process as claimed in claim 1 wherein the amount of the catalyst is in the range of 10% to 30% with respect to phenol.

8. A process as claimed in claim 1 wherein the amount of keto ester is 1, 1.2, 1.5, 2.0, 3.0 equivalent with respect to one equivalent of phenol.

9. A process as claimed in claim 1 wherein the reaction is carried out in the presence of a solvent selected from the group consisting of toluene, xylene, chlorobenzene and p-chloro toluene.

10. A process as claimed in claim 1 wherein the catalyst is recycled to the reaction mixture.

* * * * *